(12) United States Patent
Smith

(10) Patent No.: US 6,776,769 B2
(45) Date of Patent: Aug. 17, 2004

(54) ANATOMICALLY CONFIGURED TUBULAR BODY OF WOVEN OR KNITTED FABRIC FOR PRESSURE SUPPORT OF ARTICULATING JOINT

(76) Inventor: Joseph Smith, 7084 Montrico Dr., Boca Raton, FL (US) 33434

( * ) Notice: Subject to any disclaimer, the term of this patent is extended or adjusted under 35 U.S.C. 154(b) by 0 days.

(21) Appl. No.: 09/798,209

(22) Filed: Mar. 5, 2001

(65) Prior Publication Data

US 2002/0123711 A1 Sep. 5, 2002

(51) Int. Cl.$^7$ .................................................. A61F 13/00
(52) U.S. Cl. ......................... 602/61; 602/53; 602/60; 602/61; 602/62; 602/64; 602/65; 602/75; 602/76
(58) Field of Search ........................... 2/239, 240, 241, 2/242; 128/870, 875, 876, 879, 881; 602/62, 63, 64, 65, 75, 76

(56) References Cited

U.S. PATENT DOCUMENTS

| | | | | |
|---|---|---|---|---|
| 3,856,008 A | * | 12/1974 | Fowler et al. ............. | 602/62 X |
| 4,027,667 A | * | 6/1977 | Swallow et al. .......... | 602/62 X |
| 4,172,456 A | * | 10/1979 | Zens ........................ | 602/62 X |
| 4,502,301 A | * | 3/1985 | Swallow et al. .......... | 602/62 X |
| 4,665,909 A | * | 5/1987 | Trainor ........................ | 602/75 |
| 5,113,877 A | | 5/1992 | Johnson, Jr. et al. | |
| 5,185,000 A | * | 2/1993 | Brandt et al. .................. | 602/63 |
| 5,263,923 A | * | 11/1993 | Fujimoto ....................... | 602/62 |
| 5,367,708 A | * | 11/1994 | Fujimoto .......................... | 2/22 |
| 5,501,659 A | | 3/1996 | Morris et al. | |
| 5,784,721 A | * | 7/1998 | Huff ................................ | 2/239 |
| 6,063,048 A | * | 5/2000 | Bodenschatz et al. ........ | 602/62 |
| 6,126,625 A | * | 10/2000 | Lundberg ..................... | 602/27 |
| 6,126,626 A | | 10/2000 | Duback et al. | |
| 6,142,966 A | * | 11/2000 | Hely ............................ | 602/64 |
| 6,149,616 A | | 11/2000 | Szlema et al. | |
| 6,287,269 B1 | * | 9/2001 | Osti et al. ..................... | 602/62 |
| 6,338,723 B1 | * | 1/2002 | Carpenter et al. ............ | 602/75 |

FOREIGN PATENT DOCUMENTS

DE 3416253 A1 * 11/1985

* cited by examiner

Primary Examiner—Kim M. Lewis

(57) ABSTRACT

An anatomically configured tubular body or ribbon of woven or knitted elastomeric yarn having concentrated pressure support means at one or more areas along said device for pressure support of an ankle, elbow, knee or wrist (hereinafter also "articulating appendage"). The device of this invention can include an anatomically configured tubular composite, comprising an essentially uniform sleeve of elastomeric yarn and a pressure concentrating means corresponding to one or more areas of said articulating appendage (hereafter also "pressure points"), so as to focus or concentrate pressure support at said pressure points. The device thus provides for both ease of attachment to the appendage and of application of differential (increased or focused) pressures to a pressure point of the affected appendage.

11 Claims, 1 Drawing Sheet

ANATOMICALLY CONFIGURED TUBULAR BODY OF WOVEN OR KNITTED FABRIC FOR PRESSURE SUPPORT OF ARTICULATING JOINT

BACKGROUND OF THE INVENTION

1. Field of the Invention

This invention relates to an article of manufacture. More specifically, this invention is directed to a device and method for supporting an articulating joint (e.g. wrist, ankle, or knee). In the preferred embodiments of this invention, the device comprises an anatomically configured tubular sleeve of woven or knitted elastomeric yarn having concentrated pressure support for an articulating joint.

2. Description of the Prior Art

The human ankle may be injured by strains, contusions, bruises, degenerative joint diseases, arthritis, and arthroscopic operations. Such injuries may cause hematomas and inflamed areas that need to be treated. In such cases, it has been found advantageous to apply a compress of some type to the injured area to effect more rapid healing, or prevent any further inflammation or injury. Typically, support for the ankle can be provided with an Ace bandage wrap, or an anatomically configured tubular device. The anatomically configured tubular device can have an opening in the device at the heal, to permit greater of lesser degree of movement of the ankle. Similarly, a wrist support may include a sleeve having one or more finger or thumb loops to prevent relative movement (creep) of the support on the wrist while in use.

A number of patents have been disclosed in the patent literature which disclose various devices for support or treatment of a weakened or injured articulating joint. The following patents are discussed in chronological order and, thus, no significance is to be attached to their order of discussion.

U.S. Pat. No. 5,113,877 (to Johnson, Jr., et al., issued May 19, 1992) discloses an improved ankle sprain management system including a thermal compress that may be used to treat an injured ankle. The improved thermal compress for treatment of an ankle injury includes a U-shaped pad having a compartment of flexible material that is divided into inner and outer compartments, each compartment having an outer wall and a common inner wall.

U.S. Pat. No. 5,501,659 (to Morris, et al., issued Mar. 26, 1996) discloses an ankle brace to be fitted about the lower leg and ankle of a wearer for inhibiting inversion and eversion of the ankle. The plantar flexion and dorsi flexion features of the brace are characterized by a rigidifying and unitizing external shell having a unitary member made of a rigid material. The shell includes a leg encircling portion at least substantially encircling the lower leg of the wearer, and ankle stays. The ankle stays extend downwardly from the leg encircling portion over the ankle and to the heel on both the medial and lateral sides of the leg. The ankle brace also features a metatarsal support extending from the region of the metatarsal over the lateral side and instep of the wearer's foot to the medial side of the shell, where the shell provides a rigid post for anchoring the metatarsal support.

U.S. Pat. No. 6,126,626 (Duback, et al., issued Oct. 3, 2000) discloses an athletic ankle brace custom-formed to the shape of a wearer's ankle. The ankle brace includes a hardenable brace panel adapted for being molded while flexible to the medial and lateral aspects of the lower leg and ankle of the wearer. Upon hardening, the molded brace panel provides a rigid custom fit for restricting inversion and eversion of the foot during wear. The brace panel defines an integrally-formed hardenable posterior heel tongue adapted for being molded while flexible to the heel of the wearer and extending under the heel to further support the ankle upon hardening.

U.S. Pat. No. 6,149,616 (to Szlema, et al., issued Nov. 21, 2000) discloses a bandage for overload symptoms, femoropatellar pain syndromes and the patella point syndrome comprising an elastic bandage cloth in tubular form with a circumferentially extending insert of a wavy knitted fabric in the front bandage portion and a pressure pad or an annular pressure pad located within the area above the patella (when the bandage is applied). The pressure pad is open towards the top and, thus, leaves the quadriceps tendon uncovered.

In all of the above and comparable devices, support to the articulating joint is provided by one or more contrivances that are engineered into the support without any thought to the complexity of manufacture or assembly, and the resultant cost to the consumer. Moreover, even the simplest of the above devices is limited in its design preference to one and possibly two joints. Accordingly, there continues to exist a need to provide a simple, yet effective device, that can be readily configured to various anatomic sites in need of support, and more particularly, to provide focused pressure support to an affected joint.

OBJECTS OF THE INVENTION

It is the object of this invention to remedy the above as well as related deficiencies in the prior art.

More specifically, it is the principal object of the present invention to provide an anatomically configured device for pressure support of an articulating joint.

It is another object of this invention to provide an anatomically configured device of woven or knitted elastomeric yarn for pressure support of an articulating joint.

It is yet another object of this invention to provide an anatomically configured device of woven or knitted elastomeric yarn for concentrated pressure support of an articulating joint.

SUMMARY OF THE INVENTION

The above and related objects are achieved by providing a device comprising an anatomically configured tubular body of woven or knitted elastomeric yarn having concentrated pressure support means coincident with one or more areas along said device for pressure support of an ankle, elbow, knee or wrist (hereinafter also "articulating appendage"). The device of this invention can include an anatomically configured tubular composite, comprising an essentially uniform sleeve of elastomeric yarn and a pressure concentrating means corresponding to one or more areas of said articulating appendage (hereafter also "pressure points"), so as to focus or concentrate pressure support at said pressure points. The device, thus, provides for both ease of attachment to the appendage and of applications of differential (increased or focused) pressures to a pressure point of the affected appendage.

In the preferred embodiments of this invention, the pressure concentrating means of the composite comprises a delimited area having a plurality of rings of elastomeric materials having relatively greater stretch resistance than the uniform sleeve with which they are combined. For example, in the case of a device for support of a wrist, the pressure concentrating means can be located either on the device just forward of the wrist on either the palm or backside of the hand.

In another of the preferred embodiments of this invention, the composite device of this invention can include multiple delimited areas along the sleeve with concentrating pressure points on the articulating appendage. For example, in the case of a device for pressure support of the ankle, the pressure support means are typically positioned to both support the Achilles tendon and the plantar of the foot.

The device of this invention can also be provided in the form of a bandage wrap (ribbon) with periodically spaced, delimited areas of pressure support means on the bandage. In such latter configuration, the bandage wrap could be pre-configured for support of a specific appendage. This latter embodiment of the invention, would permit the user to adjust the tension to his/her personal comfort level, in the case of increased tenderness or the presence of another dressing on the effected appendage.

DETAILED DESCRIPTION OF THE INVENTION INCLUDING PREFERRED EMBODIMENTS

The Figures which accompany this application, and referenced herein, depict representative embodiments of this invention. In each instance, the composite comprises a layer of woven or knitted elastomeric yarn having concentrated pressure support means arranged at pre-designated locations for pressure support an ankle, elbow, knee or wrist (hereinafter also a "articulating appendage"). The layer of woven or knitted elastomeric yarn can be anatomically configured to a particular appendage, or, in the form of a ribbon or a bandage wrap, can be applied to the affected appendage by the individual or clinician, to support an articulating appendage.

Figure 1:
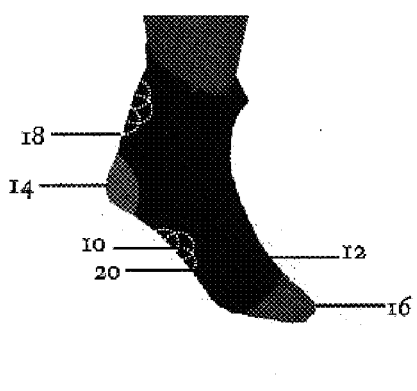
FIG. 1 is a perspective view of an ankle support device of this invention.

In FIG. 1, the device (10) of this invention is preconfigured in an anatomical shape suitable as an ankle support. The layer of material comprises a stirrup (12) with an opening at the heel (14) and at the toe (16) of the device (10). Thus, the device (10) can be slipped on as one would put on a sock. Pressure concentrating means (18, 20) are depicted on the support at the area of the device corresponding to the ankle and at the plantar of the foot, respectively. The device shown in FIG. 1, thus, wraps around the plantar of the foot and around the ankle so as to support the arch of the foot and the ankle. In this configuration, the device (10) stabilizes the ankle while not prohibiting movement for sports or normal non-athletic activities. The device (10) of FIG. 1 can thus be used for prevention, stabilization and/or to correct (relieve) sprains, or strains. The device (10) can also provide increased support, and thereby reduce swelling of the ankles, fallen arches or spurs on the inside of the heel.

Figure 2:
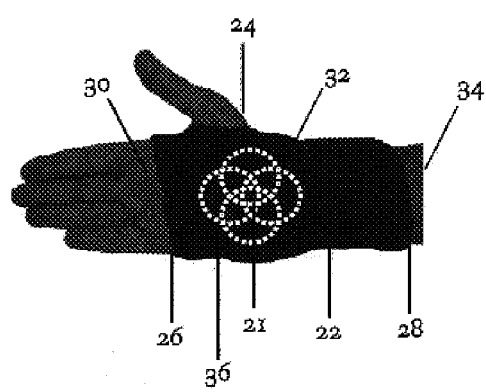
FIG. 2 is a perspective view of a wrist support device of this invention.

Similarly, in FIG. 2, the device (21) is preconfigured in an anatomical shape suitable as a wrist support. The layer of woven or knitted elastomeric yarn comprises a sleeve (22) generally conforming to a fingerless glove. The forward area of the sleeve is provided with a thumb opening (24) to anchor the sleeve (22) in position on the hand (26). The distal end (28) of the sleeve extends from the palm (30) of the hand, over the wrist (32) to the forearm (34). In the embodiment of the invention illustrated in FIG. 2, the pressure support means (36) is located on the palm-side of the sleeve (22) just forward of the wrist (32) to provide support to the carpal tunnel area of the wrist, while leaving the fingers of the hand unencumbered.

Figure 3:
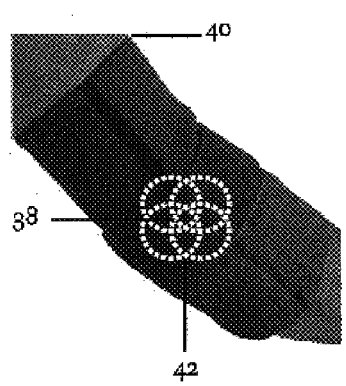
FIG. 3 is a perspective view of an elbow support device of this invention.

FIG. 3 illustrates the adaptation of the concepts of this invention to a device (38) that is anatomically configured suitable for support of an elbow. The sleeve (40) is open on each end, and a pressure support means (42) located on the sleeve approximately mid-point between each of the open ends. Although not shown, an alternative embodiment of this invention contemplates leaving an opening on the sleeve disposed opposite the pressure concentrating means to avoid discomfort or gathering of the sleeve in the crook of the elbow, when the elbow joint is flexed.

Figure 4:
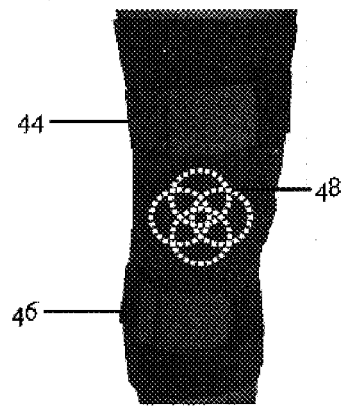
FIG. 4 is a perspective view of a bandage wrap incorporating this invention.

FIG. 4 illustrates the concept of this invention in the form of a bandage (44) comprising a ribbon (46) of woven or knitted elastomeric yarn and periodically spaced pressure concentrating means (48) positioned at pre-determined locations and/or intervals along the ribbon.

The pressure concentrating means depicted in each of the foregoing devices comprises a plurality of circular shapes of material having greater stretch resistance than the woven or knitted elastomeric yarn; or, which when combined with the woven or knitted elastomeric yarn, produce an aggregate concentrated pressure greater than the woven or knitted elastomeric yarn alone. The pressure concentrating means is formed of a pre-sewn padded, or non-padded, member that can be stitched on the sleeve or ribbon, or otherwise attached thereto. Both the relative number, and the particular form of each of the components of the pressure concentrating means can vary from that illustrated herein without departure from the spirit or scope of the concepts of this invention. Moreover, the size, shape and/or location of the components of the pressure concentrating means can include recognizable forms or logos or other configuration having one or more ornamental attributes. In each case, the combined effect of the pressure concentrating means and the woven or knitted elastomeric yarn at the pressure points on the devices of this invention is to lend additional support or focused pressure to an appendage at one or more locations on the device where such pressure concentrating means are located.

What is claimed is:

1. In an elastomeric device for pressure support of an appendage, wherein said device comprises a material anatomically configured to support a body part, the improvement comprising:
   at least one pressure concentrating means located at a pre-designated areas on said device, said pressure concentrating means comprising a plurality of overlapping circles, which when combined with said device, lends additional support or focused pressure to the body part at one or more locations on the device where said pressure concentrating means are located.

2. The improved device of claim 1, wherein said device is anatomically configured to provide increased focal support to an ankle.

3. The improved device of claim 1, wherein said device is anatomically configured to provide increased focal support to a wrist.

4. The improved device of claim 1, wherein said device is anatomically configured to provide increased focal support to an elbow.

5. The improved device of claim 1, wherein said device is anatomically configured to provide increased focal support to a knee.

6. The improved device of claim 1, wherein said device is a sleeve.

7. The improved device of claim 1, wherein device is a bandage wrap.

8. The improved device of claim 1, wherein said pressure concentrating means of said device is more stretch resistant than the material of the device.

9. The improved device of claim 1, wherein an aggregate pressure from said pressure concentrating means and said device is greater than the pressure from the device alone.

10. The improved device of claim 1, wherein said pressure concentrating means and said device are stitched together.

11. An anatomically configured device comprising:
   at least one pressure concentration means for support or focused pressure to a body part, said pressure concentrating means comprising a plurality of overlapping circles.

* * * * *